US008759321B2

(12) United States Patent
Burke et al.

(10) Patent No.: US 8,759,321 B2
(45) Date of Patent: *Jun. 24, 2014

(54) OPHTHALMIC COMPOSITION WITH HYALURONIC ACID AND POLYMERIC BIGUANIDE

(75) Inventors: Susan E. Burke, Batavia, NY (US); Srini Venkastesh, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 411 days.

This patent is subject to a terminal disclaimer.

(21) Appl. No.: 12/109,599

(22) Filed: Apr. 25, 2008

(65) Prior Publication Data
US 2008/0312182 A1 Dec. 18, 2008

Related U.S. Application Data

(60) Provisional application No. 60/943,620, filed on Jun. 13, 2007.

(51) Int. Cl.
A61L 12/14 (2006.01)

(52) U.S. Cl.
USPC .......................................................... 514/54

(58) Field of Classification Search
CPC .................................................... A61L 12/142
USPC ........................................................ 514/54
See application file for complete search history.

(56) References Cited

U.S. PATENT DOCUMENTS

| 4,141,973 | A | | 2/1979 | Balazs |
| 4,758,595 | A | | 7/1988 | Ogunbiyi et al. |
| 4,784,990 | A | * | 11/1988 | Nimrod et al. ............... 514/54 |
| 5,099,013 | A | | 3/1992 | Balazs et al. |
| 5,166,331 | A | | 11/1992 | della Valle et al. |
| 5,316,926 | A | | 5/1994 | Brown et al. |
| 5,358,706 | A | | 10/1994 | Marlin et al. |
| 5,411,874 | A | | 5/1995 | Ellwood et al. |
| 555,910 | A | | 9/1996 | Romeo et al. |
| 5,765,579 | A | | 6/1998 | Heiler et al. |
| 5,770,628 | A | | 6/1998 | Cantoro |
| 5,858,346 | A | | 1/1999 | Vehige et al. |
| 5,925,626 | A | | 7/1999 | della Valle et al. |
| 6,080,714 | A | | 6/2000 | Overkempe et al. |
| 6,277,365 | B1 | | 8/2001 | Ellis et al. |
| 6,528,465 | B1 | | 3/2003 | Cantoro |
| 6,930,077 | B2 | | 8/2005 | Glick et al. |
| 6,995,123 | B2 | | 2/2006 | Ketelson et al. |
| 7,105,473 | B2 | | 9/2006 | Glick et al. |
| 7,135,442 | B2 | | 11/2006 | Schwind et al. |
| 2002/0039975 | A1 | * | 4/2002 | Stone et al. ................... 510/112 |
| 2003/0078171 | A1 | * | 4/2003 | Tsao ............................ 510/112 |
| 2004/0063591 | A1 | | 4/2004 | Borazjani et al. |
| 2004/0253280 | A1 | | 12/2004 | Chowhan et al. |
| 2005/0054546 | A1 | * | 3/2005 | Glick et al. .................. 510/112 |
| 2005/0074467 | A1 | * | 4/2005 | Fujita et al. .................. 424/400 |
| 2005/0113425 | A1 | * | 5/2005 | Beilfuss et al. ............... 514/345 |
| 2005/0143286 | A1 | * | 6/2005 | Singh et al. .................. 514/2 |
| 2005/0152951 | A1 | | 7/2005 | Lloyd |
| 2005/0196370 | A1 | | 9/2005 | Yu et al. |
| 2005/0226841 | A1 | | 10/2005 | Yu et al. |
| 2005/0260280 | A1 | | 11/2005 | Cook et al. |
| 2005/0266089 | A1 | | 12/2005 | Cook et al. |
| 2006/0100173 | A1 | | 5/2006 | Powell et al. |
| 2007/0036829 | A1 | * | 2/2007 | Yu et al. ....................... 424/400 |
| 2007/0059276 | A1 | | 3/2007 | Bergman et al. |
| 2007/0286767 | A1 | | 12/2007 | Burke et al. |

FOREIGN PATENT DOCUMENTS

| EP | 0833609 | B1 | 11/2001 | |
| JP | 2005-346099 | A | 12/2005 | |
| JP | 2005346099 | * | 12/2005 | ............. G02C 13/00 |
| KR | 0154371 | B1 | 11/1998 | |
| WO | WO 01/057172 | | 8/2001 | |
| WO | WO 01/57172 | A1 | 8/2001 | |
| WO | WO 2008/049042 | A2 | 4/2008 | |
| WO | WO 2008/157140 | A1 | 12/2008 | |

OTHER PUBLICATIONS

Ward, K.W., "*Superficial Punctate Fluorescein Staining of the Ocular Surface*", Optometry and Vision Science 2008, 85(1) 1.
Berry et al, "Hyalruonan in dry eye and contact lens wearers," Lacrimal Gland, Tear Film, and Dry Eye Syndromes 2, Advances in Experimental Medicine and Biology, 1998, (vol. 438), (p. 785-790).
Fonn, "Targeting contact lens induced dryness and discomfort: what properties will make lenses more comfortable," Opt & Vision Sci, Apr. 2007, (vol. 84), (Issue. 4), (p. 279-285).
Frescura et al., "Evidence of hyaluronan in human tears and secretions of conjunctival cultures," Biochem Soc Transactions, 1994, (vol. 22), (p. 228S).
Fukuda et al., "Hyaluronic acid concentration in human tear fluids," Inv Oph & Visual Sci, (vol. 37), (Issue. 3), (p. S848), (Feb. 15, 1996).
Hamano et al., "Sodium hyaluronate eyedrops enhance tear film stability," Japan J Ophthal, 1996, (vol. 40), (p. 62-65).
Itoi et al., "Effect of sodium hyaluronate ophthalmic solution on peripheral staining of rigid contact lens wearers," CLAO Journal, Oct. 1995, (vol. 21), (Issue. 4), (p. 261-264).
Johnson et al., "Effectiveness of sodium hyaluronate eyedrops in the treatment of dry eye," Graefe's Arch Clin Exp Ophthalmol, 2006, (vol. 244), (p. 109-112).
Miyauchi et al., "A 26-week ophthalmic instillation test of sodium hyaluronate in rabbits," Pharmacometrics, 1993, (vol. 46), (Issue. 5), (p. 317-328).
Prabhasawat et al., "Performance profile of sodium hyalronate in patients with lipid tear deficiency: randomised, double-blind, controlled, exploratory study," Br J Ophthalmol, 2007, (vol. 91), (p. 47-50).

(Continued)

Primary Examiner — Layla Bland
Assistant Examiner — Bahar Craigo
(74) Attorney, Agent, or Firm — Toan P. Vo; Denis A. Polyn

(57) ABSTRACT

An ophthalmic composition comprising 0.5 ppm to 3 ppm of poly(hexamethylene biguanide), and 0.002 wt. % to 0.03 wt. % of hyaluronic acid. The weight ratio of hyaluronic acid to poly(hexamethylene biguanide) in the composition is from 45:1 to 120:1. The invention is also directed to a method of cleaning, disinfecting or packaging contact lenses with the composition, or to a method of rewetting contact lenses with the composition.

14 Claims, 1 Drawing Sheet

(56) References Cited

OTHER PUBLICATIONS

Pustorino et al., "Effect of bovine serum, hyaluronic acid and netilmicine on the in vitro adhesion of bacteria isolated from human-worn disposable soft contact lenses," Ann 1g, 1996, Inst of Microbiology, Italy, (vol. 8), (p. 469-475).

Sand et al., "Sodium hyaluronate in the treatment of keratoconjunctivitis sicca. A double masked clinical trial," Acta Ophthalmol, 1989, p. 181-183.

Aqua Balance, "Product Description,", 2008.

510(K) Summary of Safety and Effectiveness, "Lapis Lazuli International NV for Eye See (tm) Multipurpose, Contact Lens Solution," (Jul. 24, 2007).

Lapcik, et al., "Hyaluronan: Preparation, Structure, Properties and Application," Chemical Reviews, Dec. 1998, vol. 98 ( No. 8), p. 2663-84.

Internet Publication, "HyaCare (Novozymes)," (Jan. 14, 2008).

Hirai et al., "Effects of various lubricants on corneal surface regularity in tabbits," J Ocular Pharma and Therap, Oct. 2005, vol. 1 ( No. 5), p. 376-381.

Debbasch et al., "Cytoprotective effects of hyaluronic acid and carbomer 934P in ocular surface epithelial cells," Inv Ophthal & Visual Sci, Nov. 2002, vol. 43 ( No. 11), p. 3409-15.

Geyer et al., "A new multipurpose solution iwth hyaluronate and allantoin for all types of soft contact lenses," Lapis Lazuli Int, National Contact Lens Congress, Mar. 19-20, 2006.

EP Official Action, "EP App. 08167027.5-2123," (Jan. 19, 2010).

* cited by examiner

OPHTHALMIC COMPOSITION WITH HYALURONIC ACID AND POLYMERIC BIGUANIDE

This application claims priority to U.S. provisional application No. 60/943,620 filed Jun. 13, 2007 under 35 U.S.C. §119(e).

The present invention relates to ophthalmic compositions that comprise hyaluronic acid and a polymeric biguanide. The invention is also directed to a method of cleaning, disinfecting or packaging contact lenses with the compositions, or to a method of rewetting contact lenses with the compositions.

BACKGROUND OF THE INVENTION

During normal use contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort. Accordingly, it is important to remove such contaminants from the lens surface for continued comfortable use with a lens care solution that contains one or more cleaning components.

Ophthalmic compositions formulated as a lens care solution must also contain one or more antimicrobial components. Presently, the two most popular antimicrobial components are poly(hexamethylene biguanide), often referred to as PHMB or PAPB, and polyquaternium-1.

Lens care solutions with PHMB represent a significant improvement in patient comfort and antimicrobial effectiveness compared to most other antimicrobial components. However, as with any antimicrobial component there remains a trade-off between the concentration of the antimicrobial component in the solution and the comfort experienced by the patient. Due to its wide commercial acceptance, extensive efforts have been directed to improve the antimicrobial efficacy or the patient comfort profile by chemically modifying PHMB.

An alternative approach to improving patient comfort has been the introduction of comfort agents or hydrating agents to the lens care solutions. For example, U.S. Pat. No. 7,135,442 describes the use of dexpanthenol in combination with the sugar alcohol, sorbitol. It is said that the dexpanthenol helps to stabilize or minimize the disruption of the aqueous lachrymal layer by surfactants present in the lens care solutions.

Hyaluronic acid is a linear polysaccharide (long-chain biological polymer) formed by repeating disaccharide units consisting of D-glucuronic acid and N-acetyl-D-glucosamine linked by $\beta(1\text{-}3)$ and $\beta(1\text{-}4)$ glycosidic linkages. Hyaluronic acid is distinguished from the other glycosaminoglycans, as it is free from covalent links to protein and sulphonic groups. Hyaluronic acid is ubiquitous in animals with the highest concentration found in soft connective tissue. It plays an important role for both mechanical and transport purposes in the body, e.g., it gives elasticity to the joints and rigidity to the vertebrate disks, and it is also an important component of the vitreous body of the eye.

Hyaluronic acid, because of its high degree of hydration, is likely responsible for increasing the resistance of biological tissues or cells to compression. Also, the viscoelastic properties of hyaluronic acid, that is, hard elastic under static conditions though less viscous under small shear forces enables hyaluronic acid to basically function as a shock absorber for cells and tissues. The hyaluronic acid properties are dependent on the molecular weight, the solution concentration, and physiological pH. At low concentrations the individual chains entangle and form a continuous network in solution, which gives the system interesting properties such as pronounced viscoelasticity and pseudoplasticity that is unique for a water-soluble polymer at low concentration.

U.S. Pat. No. 5,770,628 by Cantoro describes an artificial tear composition that contains from 0.05 to 2 wt. % of hyaluronic acid. Cantoro also recognized that if one were to add a poloxamer surfactant to the artificial tear composition one could use the composition as a rewet drop. The poloxamer surfactant is said to remove denatured tear proteins and other contaminants from extended wear contact lenses while the lenses are being worn. See, U.S. Pat. No. 6,528,465.

PCT Application (Publication No. WO 01/057172) describes a multi-purpose solution to remove protein deposits from the lenses as well as to disinfect or preserve the lenses. The described solutions include a polysaccharide with a molecular weight of 5000 daltons or greater as a non-enzymatic protein remover (0.005 to 10 wt. %), a non-ionic surfactant (0.01 to 10 wt. %) and a polymeric preservative (0.00001 to 1 wt. %). An exemplary solution is provided as Example No. 5. This solution includes 0.02 wt. % sodium hyaluronate, 1.0 wt. % poloxamine (Tetronics® 1107), 0.125 wt. % $Na_2EDTA$ and 1 ppm of PHMB in a phosphate buffer.

There remains an interest and need for improved ophthalmic compositions, particularly, a multi-purpose lens care solution, that offers an improved patient comfort profile without having to sacrifice antimicrobial efficacy.

SUMMARY OF THE INVENTION

The invention is directed to an ophthalmic composition comprising 0.5 ppm to 3 ppm of poly(hexamethylene biguanide), and 0.002 wt. % to 0.03 wt. % of hyaluronic acid. The weight ratio of hyaluronic acid to poly(hexamethylene biguanide) in the composition is from 45:1 to 120:1. This composition can be used to clean and disinfect a contact lens. The method would comprise soaking or placing the contact lens in the ophthalmic composition.

The invention is also directed to an ophthalmic composition comprising 0.8 ppm to 2 ppm of poly(hexamethylene biguanide), and 0.002 wt. % to 0.02 wt. % of hyaluronic acid. The weight ratio of hyaluronic acid to poly(hexamethylene biguanide) in the composition is from 45:1 to 120:1. The ophthalmic composition also includes a boric acid/borate buffer, and a nonionic surfactant selected from poloxamer, poloxamine or any combination thereof. Again, this composition can be used to clean and disinfect a contact lens. The method would comprise soaking or placing the contact lens in the ophthalmic composition.

BRIEF DESCRIPTION OF THE FIGURES

The invention will be better understood from the following description and in consideration with the accompanying Figures. It is to be expressly understood, however, that each of the figures is provided to further illustrate and describe the invention and is not intended to further limit the invention claimed.

DETAILED DESCRIPTION OF THE INVENTION

Figure 1:
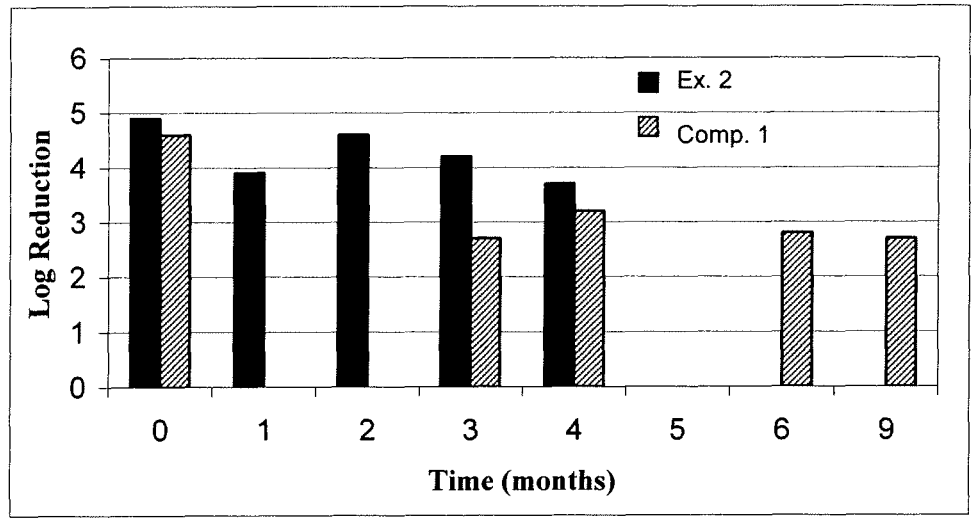
FIG. 1 is a bar graph representation of the Stand-Alone Biocidal Efficacy results of Comparative Example 1 and Example 2 with 10% organic soil (as log reduction of *S. aureus*) tested in load 4 hours after initial microbial challenge. The samples were stored in poly(ethylene terephthalate) bottles for the stated amount of time at 25° C.

Applicants and others at Bausch & Lomb have developed and tested numerous ophthalmic compositions for use as lens care solutions. Nearly all such solutions, however, fail to satisfy each and every one of the functional characteristics required of a commercially acceptable lens care solution. First, the solutions must possess the cleaning ability to remove denatured tear proteins and tear lipids as well as other external contaminants. Second, the solutions must possess significant disinfecting ability against a number of different bacteria and fungal strains for up to four months at 30° C. Third, the solutions must remain comfortable to the contact lens patient with minimal stinging as well as provide a platform to provide additional comfort or protection to the ocular surface. Fourth, the solutions must not cause significant shrinkage or swelling of the many different contact lens materials, which in turn can lead to loss in visual acuity and unwanted or pronounced lens movement. Fifth, to address market perceptions, the solutions should have a 2-hour superficial punctate corneal staining profile that equals or exceeds the staining profiles of present commercial lens care solutions. For an extensive background and review on this subject, one is referred to Ward, K. W., "*Superficial Punctate Fluorescein Staining of the Ocular Surface*", Optometry and Vision Science 2008, 85(1) 1. The ophthalmic compositions described and claimed address each of the above functional requirements as well as market perceptions regarding superficial punctate corneal staining.

Applicant's developmental program and their investigations of numerous ophthalmic formulations have led to at least two important insights. One, formulations that contain hyaluronic acid tend to exhibit less superficial punctate staining at the two-hour point than those formulations that do not contain hyaluronic acid. Two, over an extended period of time the hyaluronic acid appears to interact with cationic antimicrobial components such as PHMB and polyquaternium-1. The amount of hyaluronic acid to the amount of PHMB in the solution is critical if the commercial requirements of a contact lens solution are to be satisfied.

Accordingly, the invention is directed to an ophthalmic composition comprising 0.5 ppm to 3 ppm of PHMB and 0.002 wt. % to 0.03 wt. % of hyaluronic acid. The weight ratio of hyaluronic acid to PHMB in the composition is from 45:1 to 120:1. As defined herein, the term "hyaluronic acid" includes the corresponding metal salts of hyaluronic acid, including, for example, sodium hyaluronate (the sodium salt), potassium hyaluronate, zinc hyaluronate, magnesium hyaluronate, and calcium hyaluronate (hereafter, collectively as hyaluronic acid). It is well understood by one of ordinary skill in the art that the term "hyaluronic acid" includes the corresponding metal salts of the acid form.

The hyaluronic acid and the PHMB are each present in the ophthalmic compositions over a relatively limited concentration range. If the concentration of the hyaluronic acid is below 0.002 wt. % the commercial advantages of improved patient comfort is virtually non-existent. If on the other hand, the hyaluronic acid concentration is too high relative to the amount of PHMB present, e.g., if the hyaluronic acid concentration is about 0.02 wt. % and the PHMB concentration is about 1 to about 1.3 ppm (a calculated weight ratio of hyaluronic acid to PHMB of about 150 to 200), one begins to notice a decrease in the biocidal efficacy of the compositions over time, and in particular, with respect to the microorganism, *C. albicans*. In many of the compositions, the hyaluronic acid concentration is from 0.0075 wt. % to 0.015 wt. % and the PHMB concentration is from 0.8 ppm to 2.0 ppm.

Accordingly, the weight ratio of hyaluronic acid to PHMB is critical to maintaining patient comfort and biocidal efficacy over an extended period of time at 30° C. If the weight ratio of hyaluronic acid to PHMB is above 120, one begins to observe a decrease in biocidal efficacy over time though patient comfort is acceptable. On the other hand, if the weight ratio hyaluronic acid to PHMB is below 45, one begins to notice a decrease in patient comfort though the compositions are able to maintain the requisite biocidal properties for many months at 30° C. One of the preferred weight ratios of hyaluronic acid to PHMB is from 55:1 to 90:1. Still another preferred weight ratio of hyaluronic acid to PHMB is from 60:1 to 80:1.

Hyaluronic acid can be isolated from a variety of natural sources and is commercially available from various commercial suppliers. In its natural form, hyaluronic acid has a molecular weight in the range of $5 \times 10^4$ up to $1 \times 10^7$ daltons. Its molecular weight may be reduced via a number of cutting processes such as exposure to acid, heat (e.g. autoclave, microwave, dry heat) or ultrasound.

The isolation of hyaluronic acid from rooster combs typically includes an enzymatic digestion followed by one or more separation steps to remove proteins and provide a crude extract. Additional purification steps include precipitation in ethanol and redissolution in sodium chloride solution. Thus, a typical process for isolating hyaluronic acid from rooster comb includes removal of epithelium from the combs, grinding of combs, treatments in acetone and multiple treatments with ethanol and sodium chloride solutions. Several U.S. patents describe methods to isolate and purify hyaluronic acid including U.S. Pat. Nos. 4,141,973; 4,784,990; 5,099,013; 5,166,331; 5,316,926; 5,411,874; 5,559,104 and 5,925,626.

Alternatively, hyaluronic acid can be prepared by fermentation of bacteria such as streptococci. The bacteria are incubated in a sugar rich broth, and the produced hyaluronic acid is separated from impurities and purified. The molecular weight of hyaluronic acid produced via fermentation can be set by the sugars placed in the fermentation broth. Hyaluronic acid produced via fermentation is commercially available.

The hyaluronic acid used to prepare the compositions was obtained via a fermentation process and commercially supplied from Shandong Freda Biochem Co. Ltd., China. The hyaluronic acid produced by fermentation can have several commercial advantages over hyaluronic acid produced from extraction and purification of natural sources. Hyaluronic acid obtained from a fermentation mixture comprising *Streptococcus equi* is particularly advantageous. Also, it is advantageous that the hyaluronic acid have a glucuronic acid content that is greater than 42% by weight.

As used herein, the term "ophthalmic composition" defines a composition intended for application in the eye or intended for treating a device to be placed in contact with the eye such as a contact lens. Ophthalmic compositions can include compositions for direct placement in the eye, including eye drop solutions such as for treating dry eye and contact lens treating (rewet) solutions. Ophthalmic compositions also include those compositions formulated as multi-purpose lens care solutions for cleaning and disinfecting contact lenses or to package contact lenses.

1. The Use of the HA/PHMB Compositions in Multi-Purpose Lens Care Solutions

In addition to the presence of PHMB in the compositions, Applicants have observed that the addition of a second antimicrobial component, particularly, α-[4-tris(2-hydroxyethyl) ammonium chloride-2-butenyl]poly[1-dimethylammonium chloride-2-butenyl]-ω-tris(2-hydroxyethyl)ammonium chloride (i.e., polyquaternium-1) can provide additional biocidal properties to the compositions. For example, a preferred composition will comprise from 0.6 ppm to 1.5 ppm PHMB and from 0.5 ppm to 2 ppm as polyquaternium-1.

Another second antimicrobial component of interest is polyquaternium-42, often referred to as polixetonium. See, U.S. Pat. No. 5,300,296. Polixetonium is present in the compositions from 1 ppm to 10 ppm. For example, a preferred composition will comprise from 0.6 ppm to 1.2 ppm PHMB and from 1.5 ppm to 4 ppm as polixetonium.

The lens care solutions will very likely comprise effective amounts of one or more known lens care formulation components such as a detergent or surfactant component, a secondary comfort or wetting agent, a chelating or sequestering component, a buffer or a tonicity component.

Suitable surfactants can be either amphoteric or nonionic, and are typically present (individually or in combination) in amounts up to about 2% (w/v). The surfactant should be soluble in the lens care solution and non-irritating to ocular tissues. The presence of nonionic surfactants comprising one or more chains or polymeric components having oxyalkylene (—O—R—) repeats units wherein R has 2 to 6 carbon atoms are common to lens care solutions. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still other preferred surfactants include tyloxapol, polysulfates, polyethylene glycol, alkyl esters and any mixture thereof. The foregoing surfactants will generally be present in a total amount from 0.1% to 2% (w/v), or from 0.1% to 1.0% (w/v). Often the amount of surfactant is from 0.005% or 0.01%, to 0.1% or 0.5% or 0.8% (w/v).

A particular non-ionic surfactant consisting of a poly(oxypropylene)-poly(oxyethylene) adduct of ethylene diamine having a molecular weight from about 7,500 to about 27,000 wherein at least 40 weight percent of said adduct is poly (oxyethylene) has been found to be particularly advantageous for use in cleaning and conditioning both soft and hard contact lenses when used in amounts from about 0.05 to about 2.0 wt. %. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with Tetronic® 1107, Tetronic®1304 and Tetronic®904.

An analogous of series of surfactants, for use in the lens care compositions, is the poloxamer series which is a poly (oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237.

The amphoteric surfactants of general formula I are surface-active compounds with both acidic and alkaline properties. The amphoteric surfactants of general formula I include a class of compounds known as betaines. The betaines are characterized by a fully quaternized nitrogen atom and do not exhibit anionic properties in alkaline solutions, which means that betaines are present only as zwitterions at near neutral pH. An amphoteric surfactant of general formula I

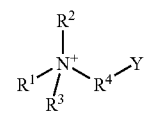

I wherein $R^1$ is R or —$(CH_2)_n$—NHC(O)R, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$, can be present in the ophthalmic compositions, typically from 0.01 wt. % to 2 wt. %. Often the amount of amphoteric surfactant is from 0.005% or 0.01%, to 0.1% or 0.5% or 0.8% (w/v).

All betaines are characterized by a fully quaternized nitrogen. In alkyl betaines, one of the alkyl groups of the quaternized nitrogen is an alkyl chain with eight to thirty carbon atoms. One class of betaines is the sulfobetaines or hydroxysulfobetaines in which the carboxylic group of alkyl betaine is replaced by sulfonate. In hydroxysulfobetaines a hydroxygroup is positioned on one of the alkylene carbons that extend from the quaternized nitrogen to the sulfonate. In alkylamido betaines, an amide group is inserted as a link between the hydrophobic $C_8$-$C_{30}$alkyl chain and the quaternized nitrogen.

In many embodiments, the amphoteric surfactant of general formula I is a sulfobetaine of general formula II

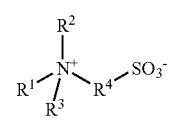

II wherein $R^1$ is a $C_8$-$C_{30}$alkyl; $R^2$ and $R^3$ are each independently selected from a $C_1$-$C_4$alkyl; and $R^4$ is a $C_2$-$C_8$alkylene.

Certain sulfobetaines of general formula II are more preferred than others. For example, Zwitergent® 93-10 available from Calbiochem Company, is a sulfobetaine of general formula I wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding Zwitergent®3-08 ($R^1$ is a is a straight, saturated alkyl with eight carbons), Zwitergent®3-12 ($R^1$ is a is a straight, saturated alkyl with twelve carbons), Zwitergent®3-14 ($R^1$ is a is a straight, saturated alkyl with fourteen carbons) and Zwitergent® 3-16 ($R^1$ is a is a straight, saturated alkyl with sixteen carbons). Accordingly, some of the more preferred the ophthalmic composition will include a sulfobetaine of general formula II wherein $R^1$ is a $C_8$-$C_{16}$alkyl and $R^2$ and $R^3$ is methyl.

In another embodiment, the amphoteric surfactant of general formula I is a hydroxysulfobetaine of general formula III

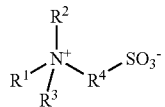

wherein $R^1$ is a $C_8$-$C_{30}$alkyl substituted with at least one hydroxyl; $R^2$ and $R^3$ are each independently selected from a $C_1$-$C_4$alkyl; and $R^4$ is a $C_2$-$C_8$alkylene substituted with at least one hydroxyl.

In another embodiment, the amphoteric surfactant is an alkylamido betaine of general formula IV

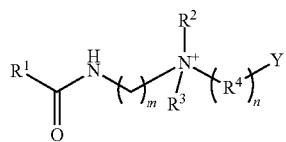

wherein $R^1$ is a $C_8$-$C_{30}$alkyl, and m and n are independently selected from 2, 3, 4 or 5; $R^2$ and $R^3$ are each independently selected from a $C_1$-$C_4$alkyl optionally substituted with hydroxyl; $R^4$ is a $C_2$-$C_8$alkylene optionally substituted with hydroxyl; and Y is $CO_2^-$ or $SO_3^-$. The most common alkylamido betaines are alkylamidopropyl betaines, e.g., cocoamidopropyl dimethyl betaine and lauroyl amidopropyl dimethyl betaine.

In addition to removing contaminants from the lens, the presence of an amphoteric surfactant of general formula I appears to counter the interaction between the hyaluronic acid and both PHMB and polyquaternium-1. The result is a lens care solution that exhibits exceptional biocidal activity and biocidal stability over time with minimal or little impact on the observed patient comfort profile that the hyaluronic acid provides. Accordingly, an amphoteric surfactant of general formula I is the surfactant of choice for the ophthalmic compositions.

The lens care solutions can also include a phosphonic acid, or its physiologically compatible salt, that is represented by the following formula:

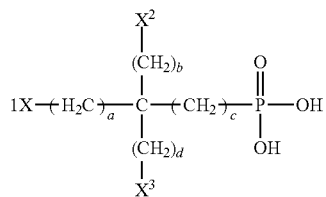

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care solutions can also include dexpanthenol, which is an alcohol of pantothenic acid, also called Provitamin B5, D-pantothenyl alcohol or D-panthenol. In some formulations of the lens care compositions, dexpanthenol can exhibit good cleansing action and can stabilize the lachrymal film at the eye surface when placing a contact lens on the eye. Dexpanthenol is preferably present in the contact lens care compositions in an amount from 0.2% to 10% (w/v), from 0.5% to 5% (w/v), or from 1% to 3% (w/v).

The lens care solutions can also include sorbitol, which is a hexavalent sugar alcohol. Typically, dexpanthenol is used in combination with sorbitol. In specific formulations the combination dexpanthenol and sorbitol can provide enhanced cleansing action and can also stabilize the lachrymal film following placement of the contact lens on the eye. These formulations can substantially improve patient comfort when wearing contact lenses. Sorbitol is present in the lens care compositions in an amount from 0.4% to 10% (w/v), from 0.8% to 6% (w/v) or from 1% to 3% (w/v).

The lens care solutions can also include one or more neutral or basic amino acids. The neutral amino acids include: the alkyl-group-containing amino acids such as alanine, glycine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1% to 5% (w/v).

The lens care solutions can also include glycolic acid, asparatic acid or any mixture of the two at a total concentration of from 0.001% to 4% (w/v) or from 0.01% to 2.0% (w/v). In addition, the combined use of one or more amino acids and glycolic acid and/or asparatic acid can lead to a reduction in the change of the size of the contact lens due to swelling and shrinkage following placement of the lens on the eye. The stated combination provides a higher degree of compatibility with the contact lens compared to the absence of one of the two components in the composition.

The lens care solutions can also include glycolic acid, asparatic acid or any mixture of the two, in combination with 2-amino-2-methyl-1,3-propanediol or a salt thereof. In some cases, solutions that contain a mixture of two of the three, or all three, compounds minimize the change of the lens size following placement of the contact lens in the eye. The 2-amino-2-methyl-1,3-propanediol (AMPD) or the salt thereof is added to the solutions in an amount to satisfy a predetermined molar ratio of glycolic acid, asparatic acid or any mixture of the two and AMPD. The molar ratio of the two components glycolic acid and/or asparatic acid to AMPD is 1:20 to 1.3:1. The glycolic acid, asparatic acid or any mixture of the two is present in the compositions at a concentration of 0.01% to 5% (w/v) or at a concentration of 0.05% to 1% (w/v).

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing a polyaminopropyl biguanide (PAPB), also known as PHMB, can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity. For example, EDTA, often used as a complexing agent, can have a noticeable effect on the buffer capacity of a solution.

A preferred buffer system is based upon boric acid/borate or a combined boric/phosphate buffer system. For example a combined boric/phosphate buffer system can be formulated from a mixture of sodium borate and phosphoric acid, or the combination of sodium borate and the monobasic phosphate.

In a combined boric/phosphate buffer system, the solution comprises about 0.05 to 2.5% (w/v) of a phosphoric acid or its salt and 0.1 to 5.0% (w/v) of boric acid or its salt. The phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

Another particular buffer system is based on diglycine. Diglycine can be used in the composition as the sole buffer system or in combination with another buffer system. The amount of diglycine or salts thereof in the composition is from 0.01 wt. % to 2 wt. %, 0.05 wt. % to 2 wt. %, 0.1 wt. % to 2 wt. % or from 0.1 wt. % to 0.5 wt. %.

The lens care solutions can also include one or more secondary comfort or wetting agents in addition to the hyaluronic acid. The secondary comfort agent can enhance and/or prolong the cleaning and wetting activity of the surfactant component and/or condition the lens surface rendering it more hydrophilic (less lipophilic) and/or to act as a demulcent on the eye.

Suitable secondary comfort or wetting agents include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include propylene glycol or glycerin. The comfort components are typically present in the solution from 0.01% to 1% (w/v).

One preferred secondary comfort agent that is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone (CAS registry number 9003-39-8). The PVP will preferably have a weight average molecular weight from 10,000 to 250,000 or from 30,000 to 100,000. Such materials are sold by various companies, including ISP Technologies, Inc. under the trademark PLASDONE® K-29/32, from BASF under the trademark KOLLIDON®, for example, KOLLIDON® K-30 or K-90. It is also preferred that one use pharmaceutical grade PVP.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator $Na_2EDTA$ or a possible combination with $Na_2EDTA$, is a disuccinate of formula IV below or a corresponding salt thereof;

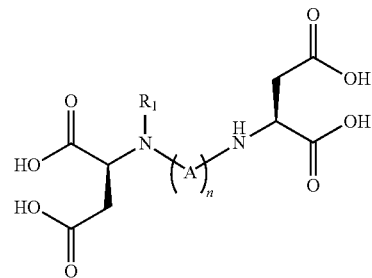

IV wherein $R_1$ is selected from hydrogen, alkyl or —C(O) alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable. Accordingly, the lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

One exemplary ophthalmic composition is formulated as a contact lens disinfecting solution prepared with the components and amounts of each listed in Table 1.

TABLE 1

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.1 |
| sodium chloride | 0.20 | 0.80 | 0.49 |
| Zwitergent ® 3-10 | 0.005 | 0.5 | 0.05 |
| hyaluronic acid | 0.005 | 0.015 | 0.01 |
| Tetronic ® 1107 | 0.05 | 2.0 | 1.00 |
| Na$_2$EDTA | 0.005 | 0.15 | 0.03 |
| PHMB | 0.2 ppm | 3 ppm | 1.3 ppm |
| polyquaternium-1 | 0.5 ppm | 5 ppm | 1 ppm |

Another contact lens solution according to the present invention includes the following ingredients listed in Table 2.

TABLE 2

| Component | Minimum Amount (wt. %) | Maximum Amount (wt. %) | Preferred Amount (wt. %) |
|---|---|---|---|
| sorbitol or xylitol | 0.5 | 5 | 3 |
| poloxamer 407 | 0.05 | 1.0 | 0.10 |
| phosphate monobasic | 0.10 | 0.8 | 0.46 |
| dexpanthenol | 0.01 | 1.0 | 0.03 |
| zwitergent ® 3-10 | 0.01 | 0.2 | 0.05 |
| hyaluronic acid | 0.005 | 0.015 | 0.01 |
| Na$_2$EDTA | 0.005 | 0.3 | 0.1 |
| PHMB | 0.2 ppm | 2 ppm | 1 ppm |

Another contact lens solution according to the present invention includes the following ingredients listed in Table 3.

TABLE 3

| Component | Minimum Amount (wt. %) | Maximum Amount (wt. %) | Preferred Amount (wt. %) |
|---|---|---|---|
| NaCl/KCl | 0.2 | 1.0 | 0.50 |
| propylene glycol | 0.1 | 1.0 | 0.50 |
| poloxamer 237 | 0.01 | 0.20 | 0.05 |
| phosphate monobasic | 0.05 | 0.40 | 0.10 |
| phosphate dibasic | 0.05 | 0.4 | 0.12 |
| hyaluronic acid | 0.005 | 0.015 | 0.008 |
| Na$_2$EDTA | 0.005 | 0.3 | 0.1 |
| PHMB | 0.2 ppm | 2 ppm | 1.1 ppm |
| polyquaternium-1 | 0.5 ppm | 5 ppm | 1 ppm |

Another contact lens solution according to the present invention includes the following ingredients listed in Table 4.

TABLE 4

| Component | Minimum Amount (wt. %) | Maximum Amount (wt. %) | Preferred Amount (wt. %) |
|---|---|---|---|
| NaCl/KCl | 0.01 | 0.5 | 0.10 |
| Tetronic ® 1304 | 0.01 | 0.2 | 0.05 |
| boric acid | 0.1 | 1.0 | 0.60 |
| sodium borate | 0.01 | 0.2 | 0.10 |
| hydroxypropyl guar | 0.01 | 0.5 | 0.05 |
| hyaluronic acid | 0.005 | 0.015 | 0.01 |
| Na$_2$EDTA | 0.02 | 0.1 | 0.05 |
| PHMB | 0.2 ppm | 2 ppm | 1 ppm |
| polyquaternium-1 | 0.5 ppm | 5 ppm | 3 ppm |

Another contact lens solution according to the present invention includes the following ingredients listed in Table 5.

TABLE 5

| Component | Minimum Amount (wt. %) | Maximum Amount (wt. %) | Preferred Amount (wt. %) |
|---|---|---|---|
| NaCl/KCl | 0.05 | 0.5 | 0.10 |
| phosphate monobasic | 0.05 | 0.40 | 0.12 |
| phosphate dibasic | 0.05 | 0.4 | 0.21 |
| sorbitol | 0.5 | 2.0 | 1.0 |
| Tetronic ® 904 | 0.02 | 0.5 | 0.10 |
| Povidone K90 | 0.05 | 0.5 | 0.10 |
| hyaluronic acid | 0.005 | 0.015 | 0.01 |
| Na$_2$EDTA | 0.005 | 0.3 | 0.1 |
| PHMB | 0.2 ppm | 2 ppm | 1 ppm |

As described, the ophthalmic compositions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is the removed from the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The formulated contact lens solutions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The ophthalmic compositions can also be formulated for use as a preservative solution or packaging solution for contact lenses. One of ordinary skill in the art would know how to adjust the formulation for each of these respective applications. The term "preservative" or "to preserve" refers to the use of the compositions for the purpose of inhibiting the growth of microorganisms in a particular product, e.g., in an eye drop formulation.

The ophthalmic compositions can be used as a preservative in ophthalmic formulations for treating patients with dry eye. In such a method, the ophthalmic formulation is administered to the patient's eye, eye lid or to the skin surrounding the patient's eye. The formulation can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

Alternatively, the ophthalmic compositions can be used as a preservative in ophthalmic formulations for treating an ocular disease or ocular condition. In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

EXAMPLES

Multipurpose Solution Formulations

A multipurpose solution were formulated with the components and amounts listed in Table 6. A compounding vessel was charged with 85 to 90 percent of the batch weight in purified water. The following materials were then added in the order listed: sodium chloride, edentate disodium, boric acid, sodium borate, hydroxyalkyl phosphonate (Dequest® 30%), and Tetronic® 1107 and the solution stirred for not less than 10 mins. The sodium hyaluronate was added to the solution at a temperature not less than 70° C. with stirring, and the solution was stirred for not less than 20 mins. The pH with was adjusted with 1N NaOH or 1N HCl if required. The solution was put through a sterilization cycle: Autoclave, 30-40 min at 121-124° C.; cool batch to less than 40° C.

An appropriate volume of purified water was charged to a second compounding vessel with a 20% w/w PHMB solution. The biguanide solution was mixed for not less than 10 mins, and transferred to the main compounding tank through a sterilizing filter (0.22 μm). If present, a measured amount of polyquaternium-1 required for the batch is added to a given amount of purified water, and the solution is stirred for at least 10 minutes. The polyquaternium-1 solution is aseptically transferred to the bulk solution through a sterilizing filter, and again the solution is stirred for at least 10 minutes.

An additional amount of water is added to bring the solution to batch weight (Q.S. to 100% w/w), and the final solution stirred for not less than 15 mins.

TABLE 6

| Component | Ex. 1 (BPZ-02) | Comp. 1 (BTH-02) | Ex. 2 (BTH-03) |
|---|---|---|---|
| boric acid | 0.64 | 0.64 | 0.64 |
| sodium borate | 0.11 | 0.11 | 0.11 |
| Dequest ® 30% | — | 0.1 | 0.1 |
| Na$_2$EDTA | 0.11 | 0.11 | 0.11 |
| Tetronic ® 1107 | 1.0 | 1.0 | 1.0 |
| Na hyaluronic acid[a] | 0.01 | 0.02 | 0.01 |
| PHMB | 1.3 | 1.3 | 1.5 |
| Polyquaternium-1 | 1.0 | — | — |
| zwitergent 3-10 | 0.05 | — | — |
| sodium chloride | 0.5 | 0.5 | 0.5 |

[a]Commercial product from Shandong Freda Biochem Co. Ltd.

Example 3

Biocidal Efficacy with Organic Soil

In order to assess the activity of the formulation, the compositions of Table 6 are bottled in 4 oz PET containers and stored at ambient temperature, as well as elevated temperatures for a given period. The stand-alone biocidal efficacy of the samples is tested at designated intervals to determine the stability of the formulation with time for is disinfection activity. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure.

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 μm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10^5$ to $1\times10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

In order to demonstrate the suitability of the medium used for growth of the test organisms and to provide an estimation of the initial inoculum concentration, inoculum controls are prepared by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0\times10^5$ and $1.0\times10^6$ cfu/mL.

The log reduction data of microorganisms determined from this testing for Example 1 (BPZ-02) is provided in Table 7.

TABLE 7

| Time (months) | Temp. ° C. | S. a. | P. a. | S. m. | C. a. | F. s. |
|---|---|---|---|---|---|---|
| 0 | 25 | 4.7 | >4.7 | 3.8 | 3.3 | >4.3 |
| 1 | 25 | 4.5 | >4.7 | 3.5 | 2.9 | 3.4 |
|   | 40 | >4.7 | >4.7 | 3.0 | 2.8 | 3.2 |
|   | 50 | 4.3 | 4.4 | 3.2 | 3.4 | 3.2 |
| 2 | 25 | >4.8 | >4.5 | 4.2 | 2.1 | 1.7 |
|   | 40 | 4.8 | >4.5 | 3.9 | 2.9 | 1.9 |
|   | 50 | >4.8 | 4.3 | 3.9 | 2.5 | 3.1 |
| 3 | 25 | >4.9 | 4.8 | 4.4 | 2.9 | 4.1 |
|   | 40 | >4.9 | >4.8 | 3.9 | 2.7 | 3.7 |
|   | 50 | >4.9 | >4.8 | 4.5 | 2.8 | 3.3 |
| 4 | 50 | >4.8 | >4.6 | >4.7 | 2.3 | 2.1 |
| OptiFree Replenish $t_0$ | 25 | 3.9 | >4.7 | 2.8 | 2.0 | 1.9 |

The log reduction data of microorganisms determined from this testing for Example 2 is provided in Table 8.

TABLE 8

| Time (months) | Temp. ° C. | S. a. | P. a. | S. m. | C. a. | F. s. |
|---|---|---|---|---|---|---|
| 0 | 25 | >4.9 | >4.6 | 4.1 | 2.7 | 4.1 |
| 1 | 25 | 3.9 | >4.7 | 3.5 | 3.4 | 3.9 |
|   | 40 | 4.0 | >4.7 | 4.1 | 3.4 | 3.4 |
|   | 50 | 4.2 | >4.7 | 3.5 | 2.8 | 3.6 |
| 2 | 25 | 4.6 | >4.7 | 4.1 | 3.2 | >4.2 |
|   | 40 | 4.5 | >4.7 | 3.5 | 2.8 | >4.2 |
|   | 50 | 3.7 | >4.7 | 3.1 | 2.4 | 3.5 |
| 3 | 25 | 4.2 | >4.6 | 4.3 | 2.7 | 3.3 |
|   | 40 | 3.5 | >4.6 | 4.4 | 2.6 | 2.6 |
|   | 50 | 2.7 | >4.6 | 4.6 | 2.4 | 2.5 |
| 4 | 25 | 3.7 | >4.7 | 4.6 | 3.7 | 3.7 |
|   | 40 | 3.3 | >4.7 | 3.9 | 3.2 | 3.6 |
|   | 50 | 2.7 | >4.7 | 3.1 | 3.1 | 2.3 |

The log reduction data of microorganisms determined from this testing for Comparative Example 2 is provided in Table 9.

TABLE 9

| Time (months) | Temp ° C. | S. a. | P. a. | S. m. | C. a. | F. s. |
|---|---|---|---|---|---|---|
| 0 | 25 | >4.6 | >4.6 | >4.7 | 2.1 | 3.0 |
| 1 | 40 | 3.9 | >4.6 | >4.9 | 1.7 | 2.7 |
| 2 | 40 | 3.0 | >4.7 | >4.6 | 2.0 | 3.2 |
| 3 | 25 | 2.7 | >4.7 | >4.7 | 1.6 | 1.9 |
|   | 40 | 2.7 | >4.7 | >4.7 | 1.4 | 1.8 |
| 4 | 25 | 3.2 | >4.6 | 4.5 | 2.6 | 3.2 |
|   | 40 | 3.1 | >4.6 | >4.5 | 2.2 | 2.0 |
| 5 | 40 | 3.2 | NT | NT | 1.4 | 1.4 |
| 6 | 25 | 2.8 | >4.6 | >4.6 | 2.4 | 3.0 |
|   | 40 | 2.4 | >4.6 | 4.5 | 1.6 | 1.2 |
| 9 | 25 | 2.7 | >4.6 | 4.7 | 2.0 | 3.5 |
|   | 40 | 2.4 | >4.6 | >4.7 | 1.2 | 1.4 |

NT—not tested

Figure 2:
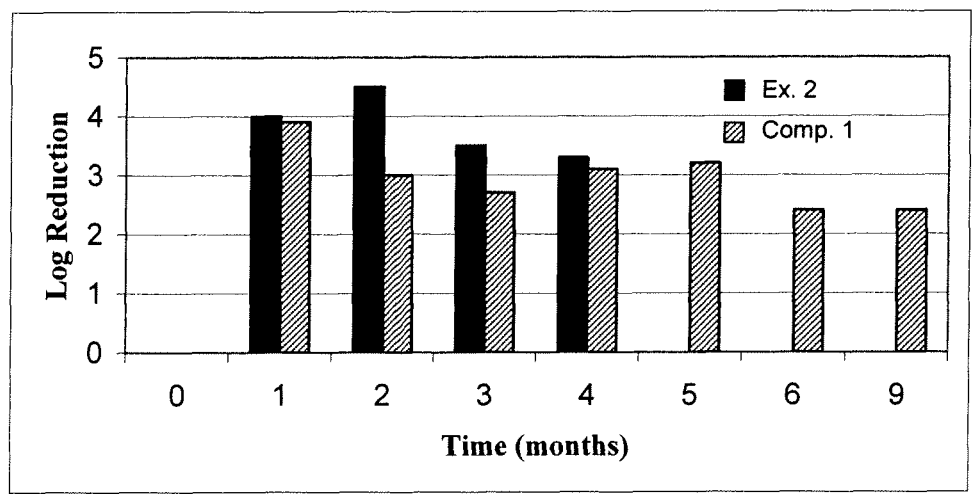
FIG. 2 is a bar graph representation of the Stand-Alone Biocidal Efficacy results of Comparative Example 1 and Example 2 with 10% organic soil (as log reduction of *S. aureus*) tested in load 4 hours after initial microbial challenge. The samples were stored in poly(ethylene terephthalate) bottles for the stated amount of time at 40° C.

FIG. 1 and FIG. 2 are bar graph representations of the stand-alone biocidal efficacy data with 10% organic soil of Comparative Example 1 and Example 2 against *S. aureus* as a function of time (months) stored at 25° C. and 40° C., respectively. The primary acceptance criteria to be considered a passing result is at least a 3 log reduction of organisms within the minimum recommended disinfection period (FDA—Premarket Notification (510(k)) Guidance Document For Contact Lens Care Products—Appendix B Disinfection Efficacy Testing). The results indicate that Comparative Example 1 does not meet the primary acceptance criteria at each time point of testing, whereas Example 2 does meet the primary acceptance criteria.

Example 4

Superficial Punctate Fluorescein Corneal Staining Clinical Procedure

A randomized, double-masked, repeated measures, contralateral eye study evaluation was conducted. Each well of the lens cases was pre-treated (a single, 4-hour minimum soak) with Example 1 or 2 (test solutions), and ReNu® Multiplus or OptiFree® Replenish (control solutions). For each case, the well treated with Example 1 or 2 was randomly determined and the opposite well received the control solution. All Bausch & Lomb PureVision lenses were pre-treated (4-hour minimum soak) with either Example 1 or 2 or with a control solution in the pre-treated lens cases, following the same randomization used for the lens case wells.

Prior to lens insertion, bulbar and limbal injection, and corneal and conjunctival staining was assessed with the slit lamp. A spherical refraction was performed, through which high contrast/high illumination (HCHI), low contrast/high illumination (LCHI) and high contrast/low illumination (HCLI) visual acuity was measured (Table 10). Each patient inserted a pre-treated test/control lens pair. Sting/burn and dryness were immediately rated. After the lenses settled, each lens was evaluated for movement, centration, comfort, wettability and deposition according to methods well recognized in the art of evaluating contact lens solutions.

A forced-choice preference for comfort was made, Table 11. A spherical over-refraction was performed, through which LogMAR visual acuity under all three testing conditions (HCHI, LCHI and HCLI) was measured. After approximately 2 hours of lens wear, each patient returned and the above tests were repeated, with the exception that the refraction and forced-preference for comfort was not repeated. Lenses were removed, corneal and conjunctival staining, and bulbar and limbal injection were reassessed, followed by reinsertion of the lenses.

For studies A, B and D lenses were worn between eight and sixteen hours per day, for three days. Every evening, just prior to lens removal, patients recorded their daily wear time; and evaluated comfort, lens cleanness and visual quality. Patients were instructed to remove their right lens and thoroughly rinse each side of the lens for 5 seconds with the solution that was assigned for the right eye, place the contact lens in the lens case and fill with the same solution. This was repeated for the left lens with the solution assigned for the left eye. Upon daily lens insertion, patients evaluated comfort, lens cleanness and visual quality on the recording forms.

The patients returned on the fourth day. At the Day 4 (am) visit, the aforementioned tests were repeated. A forced-choice preference for comfort was completed. The lenses were stored in sensitive eyes saline. The 2-way repeated measures ANOVA was used to test for differences in each of the parametric dependent variables. Non-parametric data were analyzed using the Wilcoxon Matched Pairs test. Forced-choice data was assessed using the chi-square test. Differences at the alpha=0.05 level were considered statistically significant. For study C, lenses were worn for only two hours.

TABLE 10

Corneal and Conjunctival Staining

| Study | Test Solution | control solution | # of patients | corneal staining test - (2 hr) | corneal staining control - (2 hr) |
|---|---|---|---|---|---|
| A | Comp. 1 | ReNu MultiPlus | 21 | 1.00 ± 1.14 | 1.90 ± 1.14 |
| B | Comp. 1 | Opti-Free RepleniSH | 23 | 0.91 ± 0.85 | 0.91 ± 1.31 |
| C | 2 | Opti-Free RepleniSH | 24 | 1.63 ± 1.17 | 1.13 ± 1.12 |
| D | 1 | Opti-Free RepleniSH | 23 | 1.43 ± 1.16 | 0.70 ± 0.88 |

TABLE 11

Forced-Choice Patient Comfort

| Study | Test Solution | Control Solution | # of patients | Mean comfort insertion (test) | Mean comfort insertion (control) | Mean comfort end of day (test) | Mean comfort end of day (control) |
|---|---|---|---|---|---|---|---|
| A | Comp. 1 | ReNu MultiPlus | 21 | 94.8 ± 7.1 | 95.5 ± 5.6 | 84.6 ± 17.3 | 83.6 ± 20.9 |
| B | Comp. 1 | Opti-Free RepleniSH | 23 | 96.3 ± 5.1 | 94.2 ± 11.6 | 92.9 ± 7.0 | 84.6 ± 19.9 |
| C | 2 | Opti-Free RepleniSH | 24 | 95.3 ± 6.9 | 94.2 ± 11.8 | 95.4 ± 11.8* | 93.6 ± 13.1* |
| D | 1 | Opti-Free RepleniSH | 23 | 98.3 ± 3.6 | 97.7 ± 3.9 | 89.4 ± 13.3 | 91.6 ± 10.9 |

Examples 3 and 4 and Comparative Examples 2-5

Examples 3 and 4 and Comparative Examples 2-5 listed in Table 12 are prepared in a manner described above for Examples 1 and 2.

TABLE 12

| | Example | | | | | |
|---|---|---|---|---|---|---|
| | Comp. Ex. 2 | Comp. Ex. 3 | 3 | 4 | Comp. Ex. 4 | Comp. Ex. 5 |
| boric acid | 0.64 | 0.64 | 0.64 | 0.64 | 0.64 | 0.64 |
| sodium borate | 0.12 | 0.12 | 0.12 | 0.12 | 0.12 | 0.12 |
| sodium chloride | 0.5 | 0.5 | 0.5 | 0.5 | 0.5 | 0.5 |
| $Na_2EDTA$ | 0.11 | 0.11 | 0.11 | 0.11 | 0.11 | 0.11 |
| Dequest ® 2016 | 0.1 | 0.1 | 0.1 | 0.1 | 0.1 | 0.1 |
| Tetronics ® 1107 | 1.0 | 1.0 | 1.0 | 1.0 | 1.0 | 1.0 |
| sodium hyaluronate | 0.02 | — | 0.005 | 0.01 | 0.015 | 0.02 |
| Zwitergent ® 3-10 | — | 0.1 | 0.1 | 0.1 | 0.1 | 0.1 |
| PAPB (ppm) | 1.3 | 1.0 | 1.0 | 1.0 | 1.0 | 1.0 |
| HA:PHMB | 154 | 0 | 50 | 100 | 150 | 200 |
| Stand Alone Biocidal at 4 hours | | | | | | |
| C. albicans | 1.6 | 2.7 | 2.7 | 2.1 | 1.6 | 2.0 |
| F. solani | 1.3 | 2.2 | 1.9 | 1.5 | 1.3 | 1.4 |

We claim:

1. A method of cleaning and disinfecting a contact lens, the method comprising soaking the contact lens in a multi-purpose lens care solution for at least two hours, the lens care solution comprising:

0.8 ppm to 2 ppm of poly(hexamethylene biguanide);

0.002 wt. % to 0.015 wt. % of hyaluronic acid, wherein the weight ratio of hyaluronic acid to poly(nexamethylene biguanide) in the composition is from 45:1 to 120:1; and 0.5 ppm to 2 ppm of α-[4-tris(2-hydroxyethyl)-ammonium chloride-2-butenyl]poly[1-dimethyl ammonium chloride-2-butenyl]-ω-tris(2-hydroxyethyl)ammonium Chloride, wherein the lens care solution maintains disinfecting ability against each of *S. aureus, P. aeruginosa, S. marcescens, C. albicans* and *F. solani*, for a storage time period of up to and including four months at 30° C., in accordance with FDA-Premarket Notification 510(k) Guidance Document for contact lens care products.

2. The method of claim 1 further comprising inserting the cleaned and disinfected contact lens into the eye without rinsing the lens after soaking.

3. The method of claim 1 further comprising rinsing the cleaned and disinfected contact lens with the lens care solution prior to inserting the lens into the eye.

4. The method of claim 1 wherein the hyaluronic acid has a glucuronic acid content that is greater than 42% by weight.

5. The method of claim 1 further comprising 0.01 wt. % to 0.05 wt. % ethylenediaminetetraacetic acid or a corresponding salt thereof.

6. The method of claim 1 wherein the hyaluronic acid or a salt thereof is obtained via a fermentation mixture comprising *Streptococcus* equi.

7. The method of claim 1 further comprising a disuccinate of formula IV below or a corresponding salt thereof;

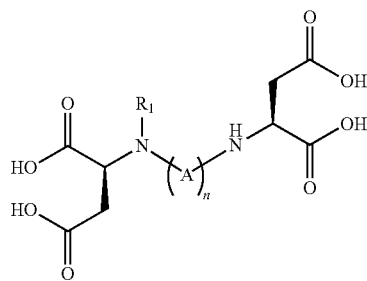

IV wherein $R_1$ is selected from hydrogen, alkyl or —C(0) alkyl, the alkyl having one to twelve carbons and optionally one or more oxygen atoms, A is a methylene group or an oxyalkylene group, and n is from 2 to 8.

8. The method of claim 1 wherein the lens care solution maintains disinfecting ability against each of *S. aureus, P. aeruginosa, S. marcescens, C. albicans* and *F. solani* for a storage time period of up to and including four months at 40° C.

9. The method of claim 1 wherein the poly(hexamethylene biguanide) is present from 1 ppm to 2 ppm, and the α-[4-tris(2-hydroxyethyl)-ammonium chloride-2-butenyl]poly[1-dimethyl ammonium chloride-2-butenyl]-ω-tris(2-hydroxyethyl)ammonium chloride is present from 1 ppm to 2 ppm.

10. The method of claim 1 wherein the lens care solution comprises diglycine, which is present at a concentration of 0.01 wt. % to 2.0 wt. %.

11. A method of cleaning and disinfecting a contact lens, the method comprising soaking the contact lens in a multipurpose lens care solution for at least two hours, the lens care solution comprising:

1 ppm to 2 ppm of poly(hexamethylene biguanide);

0.002 wt. % to 0.015 wt. % of hyaluronic acid, wherein the weight ratio of hyaluronic acid to poly(hexamethylene biguanide) in the composition is from 45:1 to 120:1;

1 ppm to 2 ppm of α-[4-tris(2-hydroxyethyl)-ammonium chloride-2-butenyl]poly[1-dimethyl ammonium chloride-2-butenyl]-ω-tris(2-hydroxyethyl)ammonium chloride, and a boron buffer component selected from the group consisting of boric acid, sodium or potassium borate, tetraborate and metaborate;

wherein the lens care solution maintains disinfecting ability against each of *S. aureus, P. aeruginosa, S. marcescens, C. albicans* and *F. solani*, for a storage time period of up to and including four months at 30° C., in accordance with FDA Premarket Notification 510(k) Guidance Document for contact lens care products.

12. The method of claim 11 wherein the lens care solution comprises diglycine, which is present at a concentration of 0.01 wt. % to 2.0 wt. %.

13. The method of claim 1 wherein the contact lens comprises a silicone hydrogel.

14. The method of claim 11 wherein the contact lens comprises a silicone hydrogel.

* * * * *